(12) United States Patent
Furukawa et al.

(10) Patent No.: US 6,365,754 B1
(45) Date of Patent: Apr. 2, 2002

(54) PROCESS FOR PRODUCING ERYTHRO-3-AMINO-2-HYDROXYBUTYRIC ACID DERIVATIVES

(75) Inventors: Yoshiro Furukawa; Keisuke Yaegashi; Kazumasa Hinoue, all of Osaka (JP)

(73) Assignee: Daiso Co., Ltd., Osaka (JP)

( * ) Notice: Subject to any disclaimer, the term of this patent is extended or adjusted under 35 U.S.C. 154(b) by 0 days.

(21) Appl. No.: 09/598,940

(22) Filed: Jun. 22, 2000

(30) Foreign Application Priority Data

Jun. 22, 1999 (JP) .......................................... 11-174967

(51) Int. Cl.$^7$ ..................... C07D 209/48; C07C 227/18; C07C 227/32; C07C 229/34
(52) U.S. Cl. .......................... 548/479; 562/39; 560/444; 558/345; 558/390
(58) Field of Search ........................... 548/479; 562/39; 560/444; 558/345, 390

(56) References Cited

U.S. PATENT DOCUMENTS

| | | | | |
|---|---|---|---|---|
| 4,391,986 A | * | 7/1983 | Umezawa et al. | 562/444 |
| 5,455,353 A | * | 10/1995 | Hilpert | 546/146 |
| 5,900,503 A | * | 5/1999 | Miyazawa et al. | 558/354 |

FOREIGN PATENT DOCUMENTS

| | | |
|---|---|---|
| EP | 0 635 493 A2 | 1/1995 |
| EP | 0 849 257 A1 | 6/1998 |
| WO | WO 95/14653 | 6/1995 |

OTHER PUBLICATIONS

Matsuda et al., *A Practical Synthesis of threo–3–Amino–2–hydroxycarboxylic Acids*, Bulletin of the Chemical Society of Japan, Japan Publications Trading Co., Tokyo, vol. 65, No. 2, Feb. 1992, pp. 360–365.

Matsuda et al., An Expeditious Synthesis of the (2R,3S)– and (2S,3R)–3–Amino–2–hydroxy–carboxylic Acids, the Key Components of a Resnin Inhibitor and Bestatin, from (S)– and (R)– Phenylalanine, Chemistry Letters, The Chemical Society of Japan, vol. 5, 1990 723–724.

Reetz et al., *Stereoselective Cyanohydrin–Forming Reactions of Chiral Alpha–Amino Aldehydes*, Tetrahedron Letters, NL, Elsevier Science Publishers, Amsterdam, vol. 29, No. 27, 1988, pp. 3295–3298.

* cited by examiner

*Primary Examiner*—Fiona T. Powers
(74) *Attorney, Agent, or Firm*—Armstrong, Westerman & Hattori, LLP

(57) ABSTRACT

The present invention relates to a process for reacting α-aminoaldehyde derivatives having a sterically bulky amino group which are commercially available with a metal cyanide in the presence of an acid chloride, an acid anhydride or the like to synthesize 3-amino-2-hydroxybutyronitrile derivatives in high yields and high erythro selectivity. When optically active α-aminoaldehyde derivatives are used, racemization hardly occurs during the reaction, and the desired products are obtained in high optical purity.

15 Claims, No Drawings

PROCESS FOR PRODUCING ERYTHRO-3-AMINO-2-HYDROXYBUTYRIC ACID DERIVATIVES

BACKGROUND OF THE INVENTION

The present invention relates to a process for producing erythro-3-amino-2-hydroxybutyric acid derivatives and esters thereof, which are useful for producing medicines, agricultural chemicals and the like, and relates to a process for producing erythro-3-amino-2-hydroxybutyronitrile derivatives, which are synthetic intermediates thereof.

3-Amino-2-hydroxybutyronitrile derivatives and 3-amino-2-hydroxybutyric acid derivatives, which are derived from them, are used as synthetic intermediates of medicines, agricultural chemicals and the like, and many processes for producing them have been reported. Among them, as processes for producing nitrile derivatives by erythro selective cyanation of α-aminoaldehyde derivatives, there have been disclosed (1) a process wherein N,N-dibenzylamino-L-phenylalaninal is reacted with trimethylsilyl cyanide in the presence of boron trifluoride etherate or zinc chloride in methylene chloride (Tetrahedron Lett., 29, 3295 (1988), WO 95/14653), (2) a process wherein aminoaldehyde derivatives are reacted with cyanohydrin derivatives in the presence of a metal compound, a base or an acid (Japanese Laid-open Patent Publication No. 231280/1998) and the like.

However, these processes for synthesis have the following problems in view of industrialization. Namely, the process (1) is unfit for large-scale synthesis since trimethylsilyl cyanide to be used as a cyanation agent is expensive and it is necessary to adjust reaction temperature to −10° C. or lower in order to obtain high selectivity. The process (2) is also unfit for large-scale synthesis since expensive aluminium reagents such as dichloroethylaluminium and triisobutylaluminium are required in order to carry out the reaction in high erythro selectivity.

SUMMARY OF THE INVENTION

Doing studies precisely to solve the above-mentioned problems, the present inventors found a process wherein erythro 3-amino-2-hydroxybutyric acid derivatives having desired configuration can be obtained simply and selectively using 2-aminoaldehyde derivatives as raw materials to accomplish the present invention.

A The present invention provides a process for producing an erythro-3-amino-2-hydroxybutyric acid derivative characterized in that a 2-aminoaldehyde derivative represented by the general formula [I]

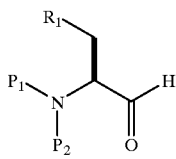

(wherein $R_1$ is a straight-chain, branched or cyclic alkyl group having one to six carbon atoms, an alkylthio group or an arylthio group having one to eight carbon atoms, or a substituted or unsubstituted aryl group, $P_1$ and $P_2$ are, the same or different, a substituted or unsubstituted aralkyl group, a substituted or unsubstituted aralkyloxycarbonyl group, a substituted or unsubstituted arylcarbonyl group, or a substituted or unsubstituted arylsulfonyl group, and $P_1$ and $P_2$ can join each other to form a substituted or unsubstituted phthaloyl or naphthaloyl ring)

is reacted with a metal cyanide in the presence of an acid chloride and/or an acid anhydride or reacted with an organic cyanide in the presence of a Lewis acid to give stereoselectively an erythro-3-amino-2-hydroxybutyronitrile derivative represented by the general formula [II]

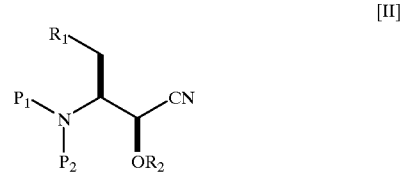

(wherein $R_1$, $P_1$ and $P_2$ are the same as mentioned above, and $R_2$ is an alkylcarbonyl group, or a substituted or unsubstituted arylcarbonyl group), and then the nitrile derivative is treated with an acid in water or in a water-containing solvent to convert it into an erythro-3-amino-2-hydroxybutyric acid derivative represented by the general formula [III]

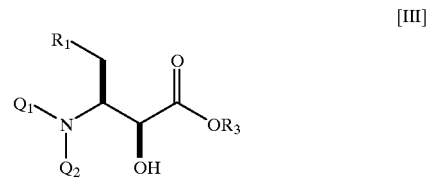

(wherein $R_1$ is the same as mentioned above, $R_3$ is hydrogen, $Q_1$ and $Q_2$ are, the same or different, hydrogen, a substituted or unsubstituted aralkyl group, or a substituted or unsubstituted arylsulfonyl group, and $Q_1$ and $Q_2$ can join each other to form a substituted or unsubstituted phthaloyl or naphthaloyl ring), or the nitrile derivative is treated with an acid in an alcoholic solvent represented by the general formula of $R_3OH$ to convert it into an ester of the butyric acid represented by the above general formula [III] (in each formula, $R_1$, $Q_1$ and $Q_2$ are the same as mentioned above, and $R_3$ is a straight-chain, branched or cyclic alkyl group having one to six carbon atoms, or a substituted or unsubstituted aralkyl group).

The reaction steps of the present invention are illustrated by the following reaction formula.

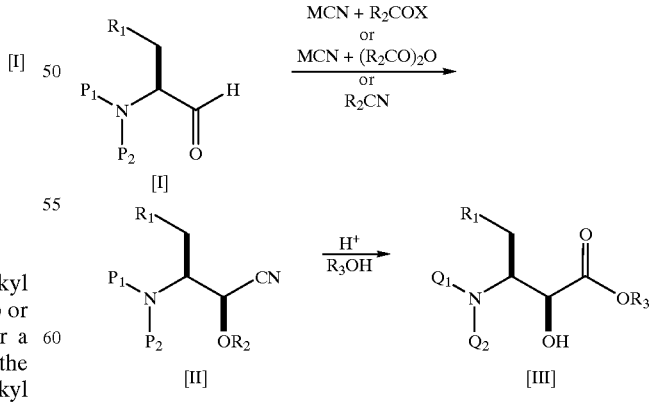

First, the first step, namely the cyanation is described.

When the 2-aminoaldehyde derivative whose amino group is protected by the bulky substituent represented by the formula [I] is cyanated, the 3-amino-2- hydroxybutyronitrile derivative [II] having erythro configuration is stereoselectively obtained. This cyanation is classified into the following two processes depending on the kind of cyanation agent to be used.

(a) When the cyanation agent is the metal cyanide, the reaction is carried out in the presence of the acid chloride and/or the acid anhydride in a two-phase solvent containing a phase-transfer catalyst.

(b) When the cyanation agent is the organic cyanide, the reaction is carried out in the presence of the Lewis acid in an aprotic solvent.

Examples of the metal cyanide to be used in the process (a) are sodium cyanide, potassium cyanide, magnesium cyanide, silver cyanide, copper cyanide and the like. Sodium cyanide and potassium cyanide are preferably used. An amount of the metal cyanide to be used is preferably one to three equivalents, more preferably one to two equivalents to a substrate (i.e. the 2-aminoaldehyde derivative [II], the same definition is applied hereinafter). Use of an excess metal cyanide does not affect a yield, but it is economically disadvantageous.

The acid chloride and/or the acid anhydride existing in the solvent in the process (a) acts as a capturing agent of alkoxide oxygen formed when the metal cyanide is added to the aldehyde as shown in the later reaction formula (A). Examples of the acid chloride are acetyl chloride, acetyl bromide, propionyl chloride, propionyl bromide, valeryl chloride, t-butylacetyl chloride, trimethylacetyl chloride, benzoyl chloride, benzoyl bromide, p-toluyl chloride, p-anisoyl chloride and the like. Acetyl chloride and benzoyl chloride are preferably used. Examples of the acid anhydride are acetic anhydride, propionic anhydride, butyric anhydride, valeric anhydride, isovaleric anhydride, trimethylacetic anhydride, benzoic anhydride, p-toluic anhydride, p-anisic anhydride and the like. Acetic anhydride and benzoic anhydride are preferably used. An amount of the acid chloride and/or the acid anhydride to be used is preferably one to three equivalents, more preferably one to two equivalents to the substrate.

Unless alkoxide oxygen of a reactive intermediate formed by stereoselective addition of the cyanide to the aldehyde, i.e. the erythro-3-amino-2-hydroxybutyronitrile derivative is successively captured immediately after generation, addition of the cyanide to the aldehyde and elimination of the cyanide from the above-mentioned reactive intermediate, which is the resulting adduct, occur reversibly and racemization proceeds remarkably as shown in the following reaction formula (B). Accordingly, it is effective to add the capturing agent in order to obtain the product in high erythro configuration selectivity.

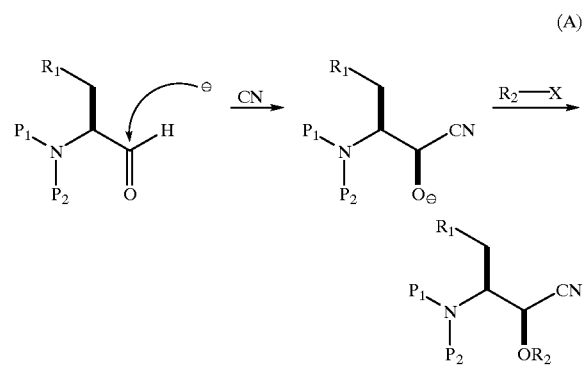

(A)

-continued

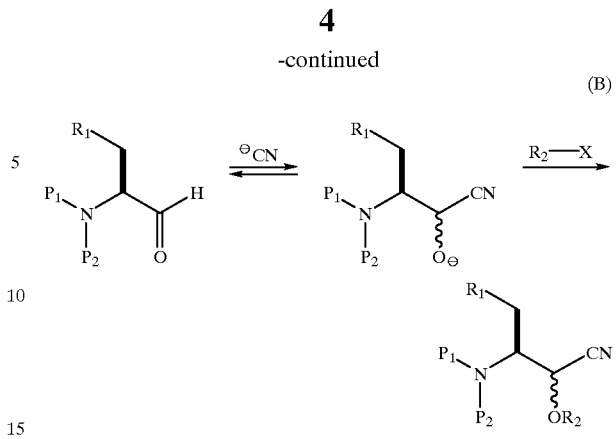

(B)

A preferred reaction solvent of the process (a) is the two-phase solvent consisting of water and a water-insoluble organic solvent. Examples of the water-insoluble organic solvent are hydrocarbon solvents such as n-hexane, benzene and toluene; ester solvents such as methyl acetate, ethyl acetate, propyl acetate and butyl acetate; ether solvents such as diethyl ether, methyl t-butyl ether and ethyl t-butyl ether; halogen solvents such as dichloromethane, chloroform and 1,2-dichloroethane; and mixed solvents thereof. Ethyl acetate, toluene, dichloromethane, 1,2-dichloroethane and methyl t-butyl ether are preferably used.

Reaction temperature of the process (a) is preferably 0 to 50° C., more preferably 0° to 25° C. The reaction of the process (a) is usually carried out under ordinary pressure and can also be carried out under elevated pressure.

The reaction of the process (a) proceeds without a catalyst, but the reaction is promoted by adding the phase-transfer catalyst. Examples of the phase-transfer catalyst are quaternary ammonium salts such as tetrabutylammonium chloride, tetrabutylammonium bromide, benzyltrimethylammonium bromide, benzyltriethylammonium chloride, benzyltributylammonium chloride, methyltrioctylammonium chloride, tetraoctylammonium bromide and N-benzylquinium chloride; quaternary phosphonium salts such as tetrabutylphosphonium chloride, tetrabutylphosphonium bromide, tetraphenylphosphonium chloride, tetraphenylphosphonium bromide, benzyltriphenylphosphonium chloride and benzyltriphenylphosphonium bromide; and crown ethers such as 12-crown-4, 15-crown-5 and 18-crown-6. Tetrabutylammonium bromide and benzyltributylammonium chloride are preferably used. An amount of the phase-transfer catalyst to be added is preferably 0.05 to 1.1 equivalents to the substrate.

Next, the above-mentioned process (b) is described.

Examples of the organic cyanide to be used in the process (b) are acyl cyanides such as acetyl cyanide, benzoyl cyanide and 4-methyl-2-oxopentanenitrile; and cyanoformates such as methyl cyanoformate and ethyl cyanoformate. An amount of the organic cyanide to be used is preferably one to three equivalents, more preferably one to two equivalents to the substrate. Use of an excess organic cyanide does not affect the yield, but it is economically disadvantageous.

Since the organic cyanide plays also a role as a capturing agent of alkoxide oxygen formed when the organic cyanide is added to the aldehyde in the process (b), it is unnecessary to add the capturing agent such as the acid chloride or the acid anhydride.

The Lewis acid catalyzes the present reaction of the process (b). Examples of the Lewis acid are zinc chloride, zinc bromide, boron trifluoride etherate, aluminium chloride, tin tetrachloride, titanium tetrachloride and the like. Zinc chloride and zinc bromide are preferably used. An amount of the Lewis acid to be added is preferably 0.05 to 1.1 equivalents to the substrate.

The reaction solvent of the process (b) is preferably the aprotic solvent. Examples of the solvent are hydrocarbon solvents such as n-h exane, benzene and toluene; ester solvents such as methyl acetate, ethyl acetate, propyl acetate and butyl acetate; ether solvents such as diethyl ether, methyl t-butyl ether, ethyl t-butyl ether, tetrahydrofuran, 1,4-dioxane, glyme, diglyme and triglyme; halogen solvents such as dichloromethane, chloroform and 1,2-dichloroethane; aprotic polar solvents such as N,N-dimethylformamide, dimethyl sulfoxide and hexamethylphosphoric triamide; nitrile solvents such as acetonitrile; and mixed solvents thereof. Tetrahydrofuran, 1,4-dioxane and N,N-dimethylformamide are more preferably used.

Reaction temperature of the process (b) is preferably −20° to 50° C., more preferably 0° to 25° C. The reaction of the process (b) is usually carried out under ordinary pressure and can also be carried out under elevated pressure.

When optically active 2-aininoaldehyde derivatives are used as raw materials of the processes (a) and (b), optically active wherein the 2-aminoaldehyde derivative is an optically active substance, and the produced erythro-3-amino-2-hydroxybutyronitrile derivative is an optically active substance.

Next, the substituents $P_1$, $P_2$, $R_1$ and $R_2$ of the compound [I] and the compound [II] in the first step are described.

The groups $P_1$ and $P_2$, which are protective groups of the amino group, can be the same or different. Examples of the groups are the substituted or unsubstituted aralkyl groups such as benzyl, triphenylmethyl, di(4-methoxyphenyl) methyl and (4-methoxyphenyl)diphenylmethyl groups; the substituted or unsubstituted aralkyloxycarbonyl groups such as benzyloxycarbonyl, p-methoxybenzyloxycarbonyl and p-nitrobenzyloxycarbonyl groups; the substituted or unsubstituted arylcarbonyl groups such as benzoyl, p-toluyl, p-anisoyl and p-phenylbenzoyl groups; and the substituted or unsubstituted arylsulfonyl groups such as benzenesulfonyl, p-toluenesulfonyl, 4-methoxybenzenesulfonyl and m-nitrobenzenesulfonyl groups. $P_1$ and $P_2$ can join each other to form the substituted or unsubstituted phthaloyl or naphthaloyl rings such as phthaloyl, 4-methylphthaloyl, 4-nitrophthaloyl, 1,8-naphthaloyl and 4-nitro-1,8-naphthaloyl groups. These groups are bulky secondary amino groups.

Examples of the substituent $R_1$ are the straight-chain, branched or cyclic alkyl groups having one to six carbon atoms such as methyl, ethyl, isopropyl, isobutyl, t-butyl and cyclohexyl groups; the alkylthio or arylthio groups such as methylthio, ethylthio and phenylthio groups; and the substituted or unsubstituted aryl groups such as phenyl, p-methoxyphenyl, p-chlorophenyl and p-nitrophenyl groups.

The substituent $R_2$ corresponds to an alkylcarbonyl group or an arylcarbonyl group of the acid chloride or the acid anhydride to be used as the capturing agent in the process (a) or an alkylcarbonyl group or an arylcarbonyl group of the organic cyanide to be used in the process (b). Specific examples of the substituent are the alkylcarbonyl groups such as acetyl, propionyl, valeryl, t-butylacetyl and trimethylacetyl groups, and the substituted or unsubstituted arylcarbonyl groups such as benzoyl, p-toluyl and p-anisoyl groups.

The intermediate [II] obtained in the first step can be purified and then used in the second step or can be used in the second step without purification.

Next, the second step, namely the acid treatment is described.

First, the conversion of the intermediate [II] into the carboxylic acid is described.

In order to convert the intermediate en erythro-3-amino-2-hydroxybutyronitrile derivative [II] into the corresponding carboxylic acid (corresponding to a compound whose $R_3$ is hydrogen in the formula [III]), the above-mentioned reaction is carried out in water or the water-containing solvent using 0.5 to 12 N hydrochloric acid or 0.5 to 36 N sulfuric acid as the acid. The above-mentioned reaction can also be carried out by dissolving, suspending or emulsifying the intermediate [II] in water or the water-containing solvent and then bubbling a hydrogen chloride gas through the liquid, or adding the intermediate [II] to water or the water-containing solvent saturated with hydrogen chloride by bubbling in advance. The water-containing solvent means a mixture of water and an organic solvent. Proportion of water is not limited, and it is, for example, 20% by weight or higher, preferably 30% by weight or higher. When the intermediate [II] is water-insoluble, the organic solvent dissolves it and makes the above-mentioned reaction proceed. The water-containing solvent at least has proportion of the organic solvent to enable this action.

Examples of the organic solvent constituting the water-containing solvent are hydrocarbon solvents such as n-hexane, benzene and toluene; ester solvents such as methyl acetate, ethyl acetate, propyl acetate and butyl acetate; ether solvents such as diethyl ether, methyl t-butyl ether, ethyl t-butyl ether, tetrahydrofuran, 1,4-dioxane, glyme, diglyme and triglyme; halogen solvents such as dichloromethane, chloroform and 1,2-dichloroethane; aprotic polar solvents such as N,N-dimethylformamide, dimethyl sulfoxide and hexamethylphosphoric triamide; nitrile solvents such as acetonitrile; and mixed solvents thereof.

Next, the conversion of the intermediate into the ester is described.

In order to convert the intermediate erythro-3-amino-2-hydroxybutyronitrile derivative [II] into the ester thereof, the nitrile derivative [II] is dissolved, suspended or emulsified in the alcoholic solvent and a hydrogen chloride gas is bubbled through the liquid, or the nitrile derivative [II] is added to the alcoholic solvent saturated with hydrogen chloride in advance. The alcoholic solvent means a solvent consisting of alcohol alone or mainly alcohol.

Examples of the alcohol to be used are straight-chain, branched or cyclic alkyl alcohols having one to six carbon atoms such as methyl alcohol, ethyl alcohol, n-propyl alcohol, isopropyl alcohol, t-butyl alcohol, n-pentyl alcohol, 1-methylbutyl alcohol, 3-methylbutyl alcohol, 1,2-dimethylpropyl alcohol, 2,2-dimethylpropyl alcohol and 1-ethylpropyl alcohol, and substituted or unsubstituted aralkyl alcohols such as benzyl alcohol.

Reaction temperature of the second step is not particularly limited, and it is usually preferably room temperature to 100° C. The reaction of the second step is usually carried out under ordinary pressure and can also be carried out under elevated pressure.

After the second step is finished, the desired compound [III] can be collected by a conventional method. For example, when the solvent is evaporated from the reaction mixture, the desired compound is obtained in the form of a salt such as a hydrochloride or a sulfate. Then, the desired compound [III] can be obtained in a desalted form by adding an aqueous alkali solution and the like to the compound to neutralize it, extracting the whole with an organic solvent which is immiscible with water and evaporating the solvent.

Furthermore, the desired compound [III] can be purified by distillation, recrystallization, chromatography or the like, if necessary.

When the optically active erythro-3-amino-2-hydroxybutyronitrile derivatives [II] are used as raw materials of the second step, optically active erythro-3-amino-2-hydroxybutyric acid derivatives or esters thereof [III] are obtained. In this case, remarkable racemization does not occur during the reaction.

The substituents $Q_1$, $Q_2$ and $R_3$ of the erythro-3-amino-2-hydroxybutyric acid derivative or the ester thereof [III] are described.

The substituent $R_3$ is hydrogen, the straight-chain, branched or cyclic alkyl group having one to six carbon atoms, or the substituted or unsubstituted aralkyl group. The alkyl group or the aralkyl group corresponds to an alkyl site or an aralkyl site of the alcohol $R_3OH$ to be used as the reaction solvent.

The substituents $Q_1$ and $Q_2$ can be the same or different. When the substituents $P_1$ and $P_2$ of the nitrile derivative [II] remain as they are without elimination even by the above-mentioned acid treatment, $Q_1$ and $Q_2$ are the substituted or unsubstituted aralkyl groups such as a benzyl group; or the substituted or unsubstituted arylsulfonyl groups such as benzenesulfonyl, p-toluenesulfonyl, 4-methoxybenzenesulfonyl and m-nitrobenzenesulfonyl groups. $Q_1$ and $Q_2$ can join each other to form the substituted or unsubstituted phthaloyl or naphthaloyl rings such as phthaloyl, 4-methylphthaloyl, 4-nitrophthaloyl, 1,8-naphthaloyl and 4-nitro-1,8-naphthaloyl groups. When the substituents $P_1$ and $P_2$ are eliminated by the above-mentioned acid treatment, $Q_1$ and $Q_2$ are hydrogen. The aralkyloxycarbonyl group and the arylcarbonyl group of the substituents $P_1$ and $P_2$ are eliminated by the above-mentioned acid treatment.

EXAMPLES

The present invention is practically described by the following Examples, but the present invention is not limited to these Examples.

Example 1

Production of (2S, 3S)-3-N,N-dibenzylamino-2-acetyloxy-4-phenylbutyronitrile

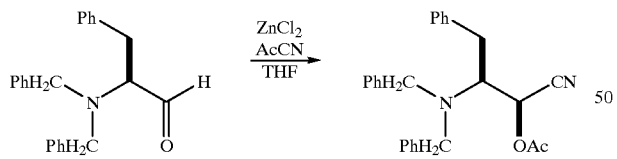

Acetyl cyanide (5.15 ml, 72.7 mmol) was added to a mixture of N,N-dibenzyl-L-phenylalaninal (20.0 g, 60.7 mmol), zinc chloride (9.91 g, 72.7 mmol) and tetrahydrofuran (70 ml) at 5° C. with stirring, and the whole was stirred at 25° C. for 12 hours. After the reaction was finished, tetrahydrofuran was evaporated under reduced pressure. Water was added to the residue, and the whole was extracted with ethyl acetate. The organic layer was washed with water, dried over anhydrous sodium sulfate and concentrated under reduced pressure. The residue was purified by silica gel column chromatography to give 20.3 g (yield 84%, erythro:threo=93:7) of titled (2S, 3S)-3-N,N-dibenzylamino-2-acetyloxy-4-phenylbutyronitrile.

Example 2

Production of Methyl (2S, 3S)-3-N,N-dibenzylamino-2-hydroxy-4-phenylbutyrate

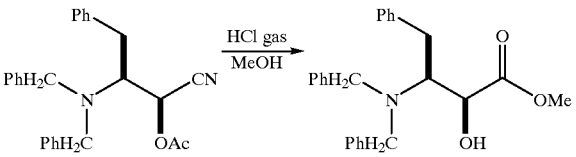

A hydrogen chloride gas was bubbled through a mixture of (2S, 3S)-3-N,N-dibenzylamino-2-acetyloxy-4-phenylbutyronitrile (20.0 g, 50.2 mmol) and methanol (50 ml) at 5° C. with stirring to saturate the mixture, and then the whole was stirred at 25° C. for 16 hours. After an excess hydrogen chloride gas was evaporated under reduced pressure, water (50 ml) was added to the mixture, and stirring was continued at 50° C. for two hours. After the reaction was finished, the reaction mixture was neutralized with sodium hydrogencarbonate, and the whole was extracted with ethyl acetate. The organic layer was washed with water, dried over anhydrous sodium sulfate and concentrated under reduced pressure. The residue was purified by silica gel column chromatography to give 16.8 g (yield 86%) of titled methyl (2S, 3S)-3-N,N-dibenzylamino-2-hydroxy-4-phenylbutyrate.

Example 3

Production of (2S, 3S)-3-N,N-dibenzylamino-2-hydroxy-4-phenylbutyric Acid

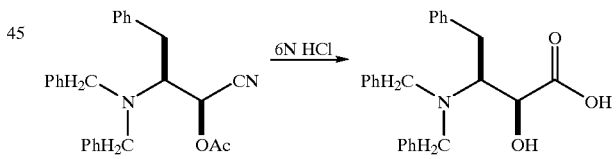

A 6 N aqueous hydrochloric acid solution (50 ml) was added to a mixture of (2S, 3S)-3-N,N-dibenzylamino-2-acetyloxy-4-phenylbutyronitrile (20.0 g, 50.2 mmol) and ethyl acetate (50 ml) at 5° C. with stirring, and then the whole was stirred at 50° C. for 15 hours. After the reaction was finished, an aqueous sodium hydroxide solution was added to the reaction mixture to adjust pH to about 3, and the whole was extracted with ethyl acetate. The organic layer was washed with water, dried over anhydrous sodium sulfate and concentrated under reduced pressure. The residue was purified by silica gel column chromatography to give 15.3 g (yield 81%) of titled (2S, 3S)-3-N,N-dibenzylamino-2-hydroxy-4-phenylbutyric acid.

Example 4

Production of (2S, 3S)-3-[N-(benzyl)-N-(benzyloxycarbonyl)amino]-2-acetyloxy-4-phenylbutyronitrile

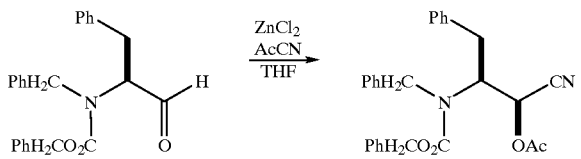

Acetyl cyanide (4.55 ml, 64.3 mmol) was added to a mixture of N-benzyl-N-benzyloxycarbonyl-L-phenylalaninal (20.0 g, 53.6 mmol), zinc chloride (8.76 g, 64.3 mmol) and tetrahydrofuran (70 ml) at 5° C. with stirring, and the whole was stirred at 25° C. for 12 hours. After the reaction was finished, tetrahydrofuran was evaporated under reduced pressure. Water was added to the residue, and the whole was extracted with ethyl acetate. The organic layer was washed with water, dried over anhydrous sodium sulfate and concentrated under reduced pressure. The residue was purified by silica gel column chromatography to give 19.6 g (yield 83%, erythro:threo=94:6) of titled (2S, 3S)-3-[N-(benzyl)-N-(benzyloxycarbonyl)amino]-2-acetyloxy-4-phenylbutyronitrile.

Example 5

Production of Ethyl (2S, 3S)-3-N-benzylamino-2-hydroxy-4-phenylbutyrate

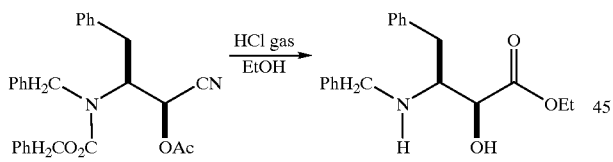

A hydrogen chloride gas was bubbled through a mixture of (2S, 3S)-3-[N-(benzyl)-N-(benzyloxycarbonyl)aminol]-2-acetyloxy-4-phenylbutyron itrile (10.0 g, 22.6 mmol) and ethanol (30 ml) at 5° C. with stirring to saturate the mixture, and then the whole was stirred at 25° C. for 14 hours. After an excess hydrogen chloride gas was evaporated under reduced pressure, water (30 ml) was added to the mixture, and stirring was continued at 50° C. for two hours. After the reaction was finished, the reaction mixture was neutralized with sodium hydrogencarbonate, and the whole was extracted with ethyl acetate. The organic layer was washed with water, dried over anhydrous sodium sulfate and concentrated under reduced pressure. The residue was purified by silica gel column chromatography to give 5.7 g (yield 80%) of titled ethyl (2S, 3S)-3-N-benzylamino-2-hydroxy-4-phenylbutyrate.

Example 6

Production of (2S, 3S)-3-N-phthaloylamino-2-acetyloxybutyronitrile

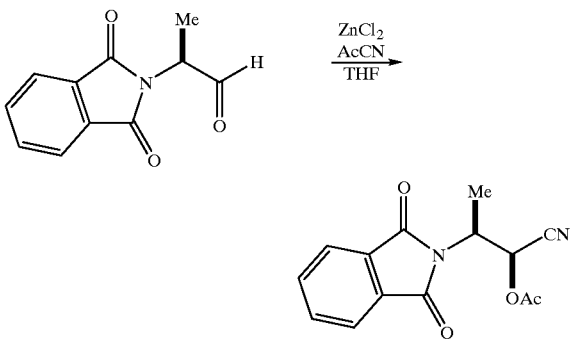

Acetyl cyanide (8.37 ml, 118.1 mmol) was added to a mixture of N-phthaloyl-L-alaninal (20.0 g, 98.4 mmol), zinc chloride (16.11 g, 118.1 mmol) and tetrahydrofaran (70 ml) at 5° C. with stirring, and the whole was stirred at 25° C. for 15 hours. After the reaction was finished, tetrahydrofuran was evaporated under reduced pressure. Water was added to the residue, and the whole was extracted with ethyl acetate. The organic layer was washed with water, dried over anhydrous sodium sulfate and concentrated under reduced pressure. The residue was purified by silica gel column chromatography to give 23.3 g (yield 87%, erythro:threo=90:10) of titled (2S, 3S)-3-N-phthaloylamino-2-acetyloxybutyronitrile.

Example 7

Production of Methyl (2S, 3S)-3-N-phthaloylamino-2-hydroxybutyrate

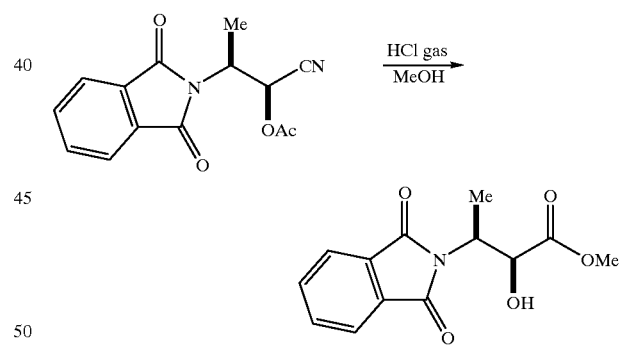

A hydrogen chloride gas was bubbled through a mixture of (2S, 3S)-3-N-phthaloylamino-2-acetyloxybutyronitrile (10.0 g, 36.7 mmol) and methanol (30 ml) at 5° C. with stirring to saturate the mixture, and then the whole was stirred at 25° C. for 16 hours. After an excess hydrogen chloride gas was evaporated under reduced pressure, water (30 ml) was added to the mixture, and stirring was continued at 50° C. for two hours. After the reaction was finished, the reaction mixture was neutralized with sodium hydrogencarbonate, and the whole was extracted with ethyl acetate. The organic layer was washed with water, dried over anhydrous sodium sulfate and concentrated under reduced pressure. The residue was purified by silica gel column chromatography to give 8.6 g (yield 89%) of titled methyl (2S, 3S)-3-N-phthaloylamino-2-hydroxybutyrate.

Example 8

Production of (2S, 3S)-3-N,N-dibenzylamino-2-benzoyloxy-4-phenylbutyronitrile

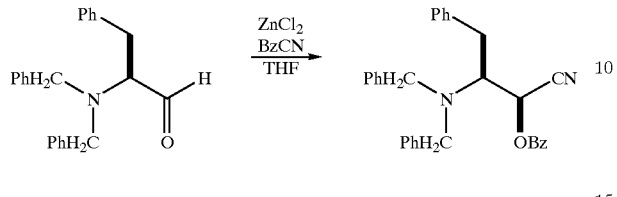

Benzoyl cyanide (8.62 ml, 72.7 mmol) was added to a mixture of N, N-dibenzyl-L-phenylalaninal (20.0 g, 60.7 mmol), zinc chloride (9.91 g, 72.7 mmol) and tetrahydrofuran (70 ml) at 5° C. with stirring, and the whole was stirred at 25° C. for 18 hours. After the reaction was finished, tetrahydrofuran was evaporated under reduced pressure. Water was added to the residue, and the whole was extracted with ethyl acetate. The organic layer was washed with water, dried over anhydrous sodium sulfate and concentrated under reduced pressure. The residue was purified by silica gel column chromatography to give 22.6 g (yield 81%, erythro:threo=85:15) of titled (2S, 3S)-3-N,N-dibenzylamino-2-benzoyloxy-4-phenylbutyronitrile.

Example 9

Production of Ethyl (2S, 3S)-3-N,N-dibenzylamino-2-hydroxy-4-phenylbutyrate

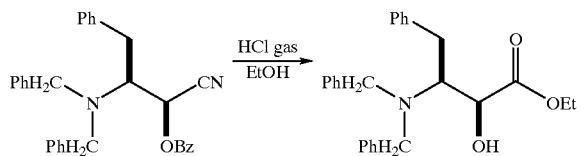

A hydrogen chloride gas was bubbled through a mixture of (2S, 3S)-3-N,N-dibenzylamino-2-benzoyloxy-4-phenylbutyronitrile (10 g, 21.7 mmol) and ethanol (30 ml) at 5° C. with stirring to saturate the mixture, and then the whole was stirred at 25° C. for 16 hours. After an excess hydrogen chloride gas was evaporated under reduced pressure, water (30 ml) was added to the mixture, and stirring was continued at 50° C. for two hours. After the reaction was finished, the reaction mixture was neutralized with sodium hydrogencarbonate, and the whole was extracted with ethyl acetate. The organic layer was washed with water, dried over anhydrous sodium sulfate and concentrated under reduced pressure. The residue was purified by silica gel column chromatography to give 7.2 g (yield 82%) of titled ethyl (2S, 3S)-3-N,N-dibenzylamino-2-hydroxy-4-phenylbutyrate.

Example 10

Production of Methyl (2S, 3S)-3-N,N-dibenzylamino-2-hydroxy-4-phenylbutyrate

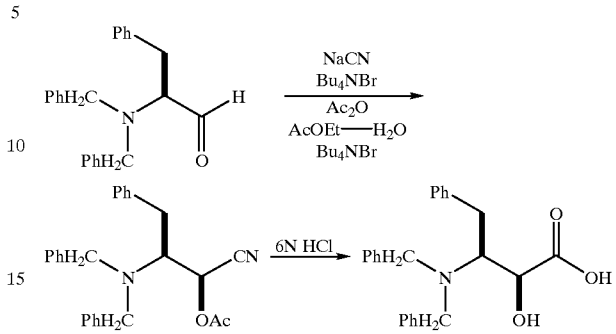

A 3 M aqueous sodium cyanide solution (12.1 ml, 36.4 mmol) was added to a mixture of N,N-dibenzyl-L-phenylalaninal (10.0 g, 30.4 mmol), tetrabutylammonium bromide (490 mg, 1.52 mmol), acetic anhydride (14.2 g, 106.2 mmol), ethyl acetate (25 ml) and water (15 ml) at 5° C. with stirring, and the whole was stirred at 25° C. for 15 hours. After the reaction was finished, an organic layer and an aqueous layer were separated. The organic layer was washed with water, dried over anhydrous sodium sulfate and concentrated under reduced pressure to give 13.3 g of a crude product containing (2S, 3S)-3-N,N-dibenzylamino-2-acetyloxy-4-phenylbutyronitrile.

Next, the crude product was dissolved in methanol (30 ml), a hydrogen chloride gas was bubbled through the resulting solution at 5° C. with stirring to saturate the solution, and the whole was stirred at 25° C. for 15 hours. After an excess hydrogen chloride gas was evaporated under reduced pressure, water (30 ml) was added to the mixture, and stirring was continued at 50° C. for two hours. After the reaction was finished, the reaction mixture was neutralized with sodium hydrogencarbonate, and the whole was extracted with ethyl acetate. The organic layer was washed with water, dried over anhydrous sodium sulfate and concentrated under reduced pressure. The residue was purified by silica gel column chromatography to give 8.6 g (yield 73%, erythro:threo=87:13) of titled methyl (2S, 3S)-3-N,N-dibenzylamino- 2-hydroxy-4-phenylbutyrate.

Example 11

Production of (2S, 3S)-3-N,N-dibenzylamino-2-hydroxy-4-phenylbutyric Acid

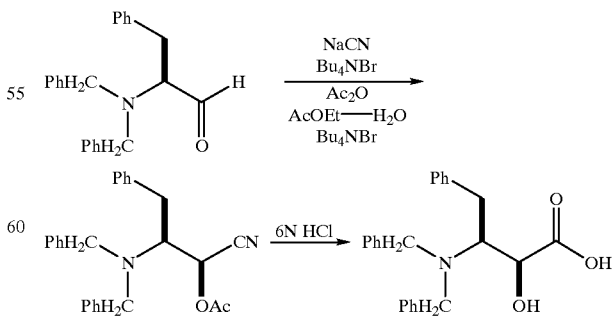

A 3 M aqueous sodium cyanide solution (12.1 ml, 36.4 mmol) was added to a mixture of N,N-dibenzyl-L- phenylalaninal (10.0 g, 30.4 mmol), tetrabutylammonium bromide (490 mg, 1.52 mmol), acetic anhydride (14.2 g, 106.2 mmol), ethyl acetate (25 ml) and water (15 ml) at 5° C. with stirring, and the whole was stirred at 25° C. for 15 hours. After the reaction was finished, an organic layer and an aqueous layer were separated. The organic layer was washed with water, dried over anhydrous sodium sulfate and concentrated under reduced pressure to give 13.5 g of a crude product containing (2S, 3S)-3-N,N-dibenzylamino-2-acetyloxy-4-phenylbutyronitrile.

Next, the crude product was dissolved in ethyl acetate (30 ml), a 6 N aqueous hydrochloric acid solution (30 ml) was added to the resulting solution at 5° C. with stirring, and the whole was stirred at 50° C. for 15 hours. After the reaction was finished, an aqueous sodium hydroxide solution was added to the reaction mixture to adjust pH to about 3, and the whole was extracted with ethyl acetate. The organic layer was washed with water, dried over anhydrous sodium sulfate and concentrated under reduced pressure. The residue was purified by silica gel column chromatography to give 8.3 g (yield 73%, erythro:threo=87:13) of titled (2S, 3S)-3-N,N-dibenzylamino- 2-hydroxy-4-phenylbutyric acid.

Example 12

Production of Ethyl (2S, 3S)-3-N-benzylamino-2-hydroxy-4-phenylbutyrate

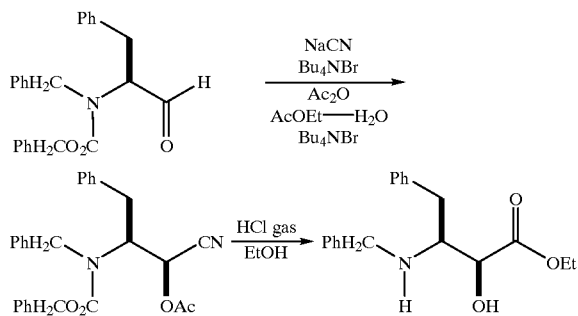

A 3 M aqueous sodium cyanide solution (21.4 ml, 64.3 mmol) was added to a mixture of N-benzyl-N-benzyloxycarbonyl-L-phenylalaninal (20.0 g, 53.6 mmol), tetrabutylammonium bromide (863 mg, 2.68 mmol), acetic anhydride (25.1 g, 187.4 mmol), ethyl acetate (50 ml) and water (30 ml) at 5° C. with stirring, and the whole was stirred at 25° C. for 16 hours. After the reaction was finished, an organic layer and an aqueous layer were separated. The organic layer was washed with water, dried over anhydrous sodium sulfate and concentrated under reduced pressure to give 25.6 g of a crude product containing (2S,3S)-3-[N-(benzyl)-N-(benzyloxycarbonyl) amino]-2-acetyloxy-4-phenylbutyronitrile.

Next, the crude product was dissolved in ethanol (50 ml), a hydrogen chloride gas was bubbled through the resulting solution at 5° C. with stirring to saturate the solution, and the whole was stirred at 25° C. for 15 hours. After an excess hydrogen chloride gas was evaporated under reduced pressure, water (50 ml) was added to the mixture, and stirring was continued at 50° C. for two hours. After the reaction was finished, the reaction mixture was neutralized with sodium hydrogencarbonate, and the whole was extracted with ethyl acetate. The organic layer was washed with water, dried over anhydrous sodium sulfate and concentrated under reduced pressure. The residue was purified by silica gel column chromatography to give 12.6 g (yield 75%, erythro:threo=88:12) of titled ethyl (2S, 3S)-3-N-benzylamino-2-hydroxy-4-phenylbutyrate.

Example 13

Production of Methyl (2S, 3S)-3-N-phthaloylamino-2-hydroxybutyrate

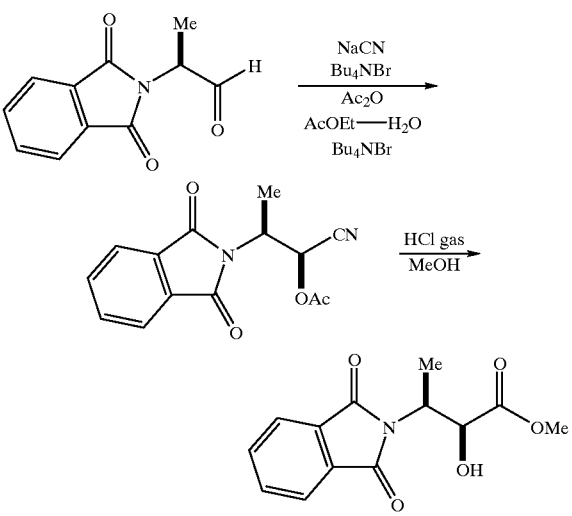

A 3 M aqueous sodium cyanide solution (19.7 ml, 59.1 mmol) was added to a mixture of N-phthaloyl-L-alaninal (10.0 g, 49.2 mmol), tetrabutylammonium bromide (793 mg, 2.46 mmol), acetic anhydride (23.1 g, 172.2 mmol), ethyl acetate (50 ml) and water (30 ml) at 5° C. with stirring, and the whole was stirred at 25° C. for 17 hours. After the reaction was finished, an organic layer and an aqueous layer were separated. The organic layer was washed with water, dried over anhydrous sodium sulfate and concentrated under reduced pressure to give 14.7 g of a crude product containing (2S, 3S)-3-N-phthaloylamino-2-acetyloxybutyronitrile.

Next, the crude product was dissolved in methanol (30 ml), a hydrogen chloride gas was bubbled through the resulting solution at 5° C with stirring to saturate the solution, and the whole was stirred at 25° C. for 17 hours. After an excess hydrogen chloride gas was evaporated under reduced pressure, water (30 ml) was added to the mixture, and stirring was continued at 50° C. for two hours. After the reaction was finished, the reaction mixture was neutralized with sodium hydrogencarbonate, and the whole was extracted with ethyl acetate. The organic layer was washed with water, dried over anhydrous sodium sulfate and concentrated under reduced pressure. The residue was purified by silica gel column chromatography to give 9.6 g (yield 74%, erythro:threo=87:13) of titled methyl (2S, 3S)-3-N-phthaloylamino-2-hydroxybutyrate.

What is claimed is:

1. A process for producing an erythro-3-amino-2-hydroxybutyric acid derivative characterized in that a 2-aminoaldehyde derivative represented by the general formula [I]

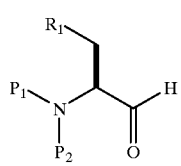

(wherein $R_1$ is a straight-chained, branched or cyclic alkyl group having one to six carbon atoms, an alkylthio group or an arylthio group having one to eight carbon atoms, or a substituted or unsubstituted aryl group, $P_1$ and $P_2$ are, the same or different, a substituted or unsubstituted aralkyl group, a substituted or unsubstituted aralkyloxycarbonyl group, a substituted or unsubstituted arylcarbonyl group, or a substituted or unsubstituted arylsulfonyl group, or $P_1$ and $P_2$ may together represent a substituted or unsubstituted phthaloyl or naphthaloyl ring) is reacted with a metal cyanide in the presence of an acid chloride and/or an acid anhydride or reacted with an organic cyanide in the presence of a Lewis acid to give stereoselectively an erythro-3-amino-2-hydroxybutyronitrile derivative represented by the general formula [II]

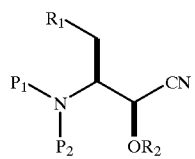

(wherein $R_1$, $P_1$ and $P_2$ are the same as mentioned above, and $R_2$ is an alkylcarbonyl group, or a substituted or unsubstituted arylcarbonyl group), and then the nitrile derivative is treated with an acid in water or in a water-containing solvent to convert it into an erythro-3-amino-2-hydroxybutyric acid derivative represented by the general formula [III]

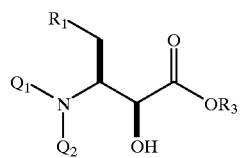

(wherein $R_1$ is the same as mentioned above, $R_3$ is hydrogen, $Q_1$ and $Q_2$ are, the same or different, hydrogen, a substituted or unsubstituted aralkyl group, or a substituted or unsubstituted arylsulfonyl group, or $Q_1$ and $Q_2$ may together represent a substituted or unsubstituted phthaloyl or naphthaloyl ring),
or the nitrile derivative is treated with an acid in an alcoholic solvent represented by the general formula or $R_3OH$ to convert it into an ester of butyric acid represented by the above general formula [III] (in each formula, $R_1$, $Q_1$ and $Q_2$ are the same as mentioned above, and $R_3$ is a straight-chain, branched or cyclic alkyl group having one to six carbon atoms, or a substituted or unsubstituted aralkyl group).

2. A process for producing an erythro-3-amino-2-hydroxybutyronitrile derivative characterized in that a 2-aminoaldehyde derivative represented by the general formula [I]

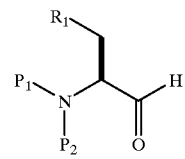

(wherein $R_1$ is a straight-chain, branched or cyclic alkyl group having one to six carbon atoms, an alkylthio group or an arylthio group having one to eight carbon atoms, or a substituted or unsubstituted aralkyl group, a substituted or unsubstituted aralkyloxycarbonyl group, a substituted or unsubstituted arylcarbonyl group, or a substituted or unsubstituted arylsulfonyl group, or $P_1$ and $P_2$ may together represent a substituted or unsubstituted phthaloyl or naphthaloyl ring) is reacted with a metal cyanide in the presence of an acid chloride and/or an acid anhydride or reacted with an organic cyanide in the presence of a Lewis acid to five stereoselectively the erythro-3-amino-2-hydroxybutyronitrile derivative represented by the general formula [II]

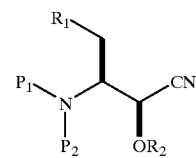

(wherein $R_1$, $P_1$ and $P_2$ are the same as mentioned above, and $R_2$ is an alkylcarbonyl group, or a substituted or unsubstituted arylcarbonyl group).

3. A process for producing an erythro-3-amino-2-hydroxybutyric acid derivative characterized in that an erythro-3-amino-2-hydroxybutyric acid derivative represented by the general formula [II]

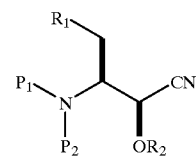

(wherein $R_1$ is a straight-chain, branched or cyclic alkyl group having one to six carbon atoms, an alkylthio group or an arylthio group having one to eight carbon atoms, or a substituted or unsubstituted aryl group, $R_2$ is an alkylcarbonyl group, or a substituted or unsubstituted arylcarbonyl group, $P_1$ and $P_2$ are, the same or different, a substituted or unsubstituted aralkyl group, a substituted or unsubstituted aralkyloxycarbonyl group, a substituted or unsubstituted arylcarbonyl group, or a substituted or unsubstituted arylsulfonyl group, or $P_1$ and $P_2$ may together represent a substituted or unsubstituted phthaloyl or naphthaloyl ring) is treated with an acid in water or in a water-containing solvent to convert it into an erythro-3-amino-2-hydroxybutyric acid derivative represented by the general formula [III]

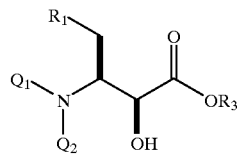

(wherein $R_1$ is the same as mentioned above, $R_3$ is hydrogen, $Q_1$ and $Q_2$ are, the same or different, hydrogen, a substituted or unsubstituted aralkyl group, or a substituted or unsubstituted arylsulfonyl group, or $Q_1$ and $Q_2$ may together represent a substituted or unsubstituted phthaloyl or naphthaloyl ring), or the nitrile derivative is treated with an acid in an alcoholic solvent represented by the general formula of $R_3OH$ to convert it into a ester of the butyric acid represented by the general formula [III] (in each formula, $R_1$, $Q_1$ and $Q_2$ are the same as mentioned above, and $R_3$ is a straight-chain, branched or cyclic alkyl group having one to six carbon atoms, or a substituted or unsubstituted aralkyl group).

4. A process for production as claimed in claim 2, wherein the cyanation with the metal cyanide is carried out in a two-phase solvent containing a phase-transfer catalyst.

5. A process for production as claimed in claim 2, wherein the metal cyanide is sodium cyanide, potassium cyanide or a mixture thereof.

6. A process for production as claimed in claim 2, wherein the acid chloride is acetyl chloride, benzoyl chloride or a mixture thereof, and the acid anhydride is acetic anhydride, benzoic anhydride or a mixture thereof.

7. A process for production as claimed in claim 4, wherein the phase-transfer catalyst is a quaternary ammonium salt.

8. A process for production as claimed in claim 4, wherein the two-phase solvent consists of ethyl acetate, toluene, dichloromethane, 1, 2-dichloroethane, methyl t-butyl ether or a mixed solvent thereof and water.

9. A process for production as claimed in claim 2, wherein the cyanation with the organic cyanide is carried out in an aprotic solvent.

10. A process for production as claimed in claim 2, wherein the organic cyanide is acetyl cyanide, benzoyl cyanide or a mixture thereof.

11. A process for production as claimed in claim 2, wherein the Lewis acid is zinc chloride, zinc bromide or a mixture thereof.

12. A process for production as claimed in claim 9, wherein the aprotic solvent is N,N-dimethylformamide, dimethyl sulfoxide, tetrahydrofuran, 1,4-dioxane or a mixture thereof.

13. A process for production as claimed in claim 3, wherein the alcohol is methyl alcohol, ethyl alcohol, n-propyl alcohol, isopropyl alcohol, t-butyl alcohol, n-pentyl alcohol, 1-methylbutyl alcohol, 3-methylbutyl alcohol, 1,2-dimethylpropyl alcohol, 2,2-dimethylpropyl alcohol, 1-ethylpropyl alcohol or benzyl alcohol.

14. A process for production as claimed in any one of claims 1, 2 and 4, wherein the 2-aminoaldehyde derivative is an optically active substance, and the produced erythro-3-amino-2-hydroxybutyronitrile derivative is an optically active substance.

15. A process for production as claimed in any one of claims 1, 3 and 4, wherein the erythro-3-amino-2-hydroxybutyronitrile derivative is an optically active substance, and produced erythro-3-amino-2-hydroxybutyric acid or the ester thereof is an optically active substance.

* * * * *